Figure 1:
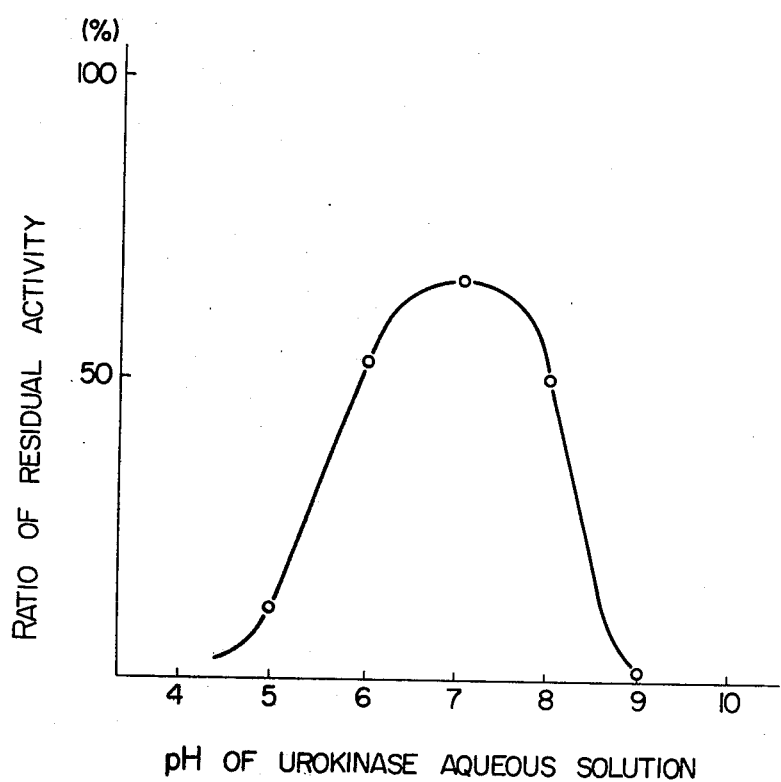

United States Patent [19]

Suyama

[11] 4,286,063

[45] Aug. 25, 1981

[54] METHOD FOR PRODUCING THROMBOLYTIC PREPARATION

[75] Inventor: Tadakazu Suyama, Kyoto, Japan

[73] Assignee: The Green Cross Corporation, Osako, Japan

[21] Appl. No.: 105,116

[22] Filed: Dec. 19, 1979

[30] Foreign Application Priority Data

Dec. 21, 1978 [GB] United Kingdom ............... 49638/78

[51] Int. Cl.$^3$ ............................................. C12N 9/72
[52] U.S. Cl. ................................... 435/215; 435/188; 435/814; 435/815
[58] Field of Search .................... 435/215, 188, 814

[56] References Cited

U.S. PATENT DOCUMENTS

| | | | |
|---|---|---|---|
| 3,950,223 | 4/1976 | Yugari et al. | 435/215 X |
| 4,066,506 | 1/1978 | Johnson et al. | 435/215 |

FOREIGN PATENT DOCUMENTS 2387241  12/1978  France ..................................... 435/215

OTHER PUBLICATIONS

White et al., Biochemistry vol. 5 No. 7, pp. 2160–2169, Jul. 1966.

*Primary Examiner*—Lionel M. Shapiro
*Attorney, Agent, or Firm*—Cushman, Darby & Cushman

[57] ABSTRACT

A method for producing a thrombolytic preparation characterized in that among treatment conditions in the urokinase production pH is maintained within the neutral or weakly alkaline range throughout each treatment step to produce a thrombolytic preparation containing urokinase having a molecular weight of 54,000±10,000 as major ingredient.

3 Claims, 2 Drawing Figures

METHOD FOR PRODUCING THROMBOLYTIC PREPARATION

This invention relates to a method for producing a thrombolytic preparation containing as major constituent urokinase having a molecular weight of 54,000±10,000.

Urokinase is an enzyme existing in minute amounts in human urine and has a function of activating plasminogen contained in serum to form plasmin having fibrinolytic activity. Being an effective activator for the fibrinolytic system, urokinase is isolated from human urine or tissue cultures of kidney and purified to be clinically used widely in treatment of various thrombosis, cancers in combination with carcinostatic agents, and other diseases.

Thus, urokinase has become very useful in the pharmaceutical field. The present inventors conducted studies to promote more efficient utilization of urokinase in its therapeutic use. The urokinase preparations currently in use as pharmaceuticals are mixtures of different molecular weights. Two types of urokinase have been known, the one having a molecular weight of about 33,000±10,000 and the other a molecular weight of about 54,000±10,000. These are mixed so as to show a definite potency. Although the reason has not yet been decided, the existence of enzymes of different molecular weight in urokinase is presumed to be ascribable to the existence of isozymes due to the difference in enzyme-producing tissues, transformation into sub-units by the action of proteolytic enzymes in urine or other materials, or decomposition and modification during the recovery from urine.

It is presumable that urokinase preparations having different molecular weights will naturally exhibit different physiological efficacy. However, neither sufficient suggestions about such a problem nor informations on significant difference in efficacy have been obtained from the conventional test in vitro by the fibrin plating method or by the two-step method [Pharmaceuticals Research, 5 (3), 295-308 (1974)] which has generally been carried out to standardize the enzymatic activity of the urokinase preparations. Consequently, in administering the urokinase preparation, standardization has been performed by adjusting the total potency by the test in vitro. In another word, urokinase was administered on the assumption that its physiological efficacy is the same if the enzymatic activity (potency) in vitro is the same, in spite of the diversity in molecular weight of urokinase.

Under the above circumstances of the art, diversity of the molecular weight of urokinase preparations was elucidated and animal tests as well as clinical uses of urokinase were extended. Just at the time, the present inventors found that there exists a not insignificant difference between the activity in vitro and the behavior in vivo of urokinase depending on the molecular weight.

Starting from the above finding, the present inventors further examined whether the enzymatic activity in vitro reflects exactly the enzymatic efficacy in vivo, whether urokinase of different molecular weight exhibits the same biological efficacy in vivo, and whether or not there exits other enzymological difference depending on the difference in molecular weight. As the result, it was surprisingly found that there exits quite a large difference with respect to thrombolytic activity among samples which have been adjusted to the same potency based on the enzymatic activity assayed by the two-step method or other methods in vitro and that there exists a certain interrelationship between the molecular weight and the thrombolytic activity of urokinase. Urokinase with a higher molecular weight was found to exhibit a higher thrombolytic effect even if the potency determined in vitro by the two-step method or other methods was the same. It was further found that urokinase with larger molecular weight is superior also in preservability.

Groups of beagles were intravenously administered with, respectively, urokinase of higher molecular weight (54,000) and urokinase of lower molecular weight (33,000) each labelled with $^{125}$I and the attenuation of each urokinase in blood was traced. It was found that the higher molecular weight urokinase remains longer in the blood and its half-life reaches about twice that of the lower molecular weight one.

Figure 2:
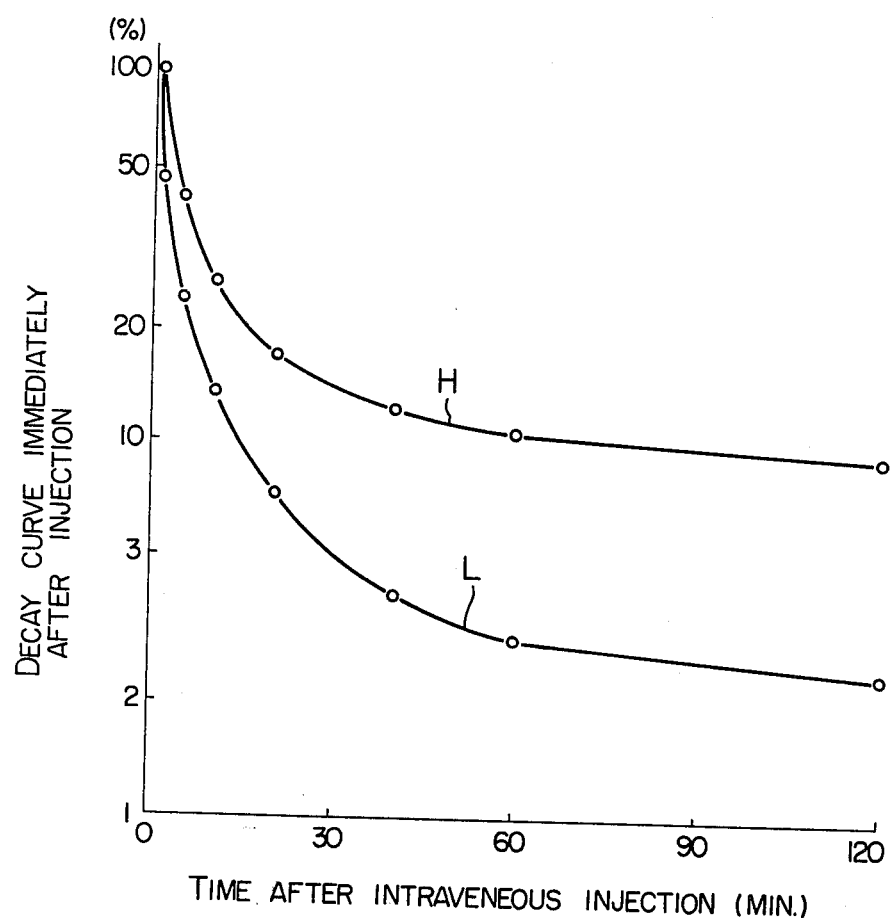

In the accompanying drawings,

FIG. 1 is a diagram representing the relationship between pH of an aqueous solution of urokinase and the ratio of residual activity; and FIG. 2 is diagrams representing the attenuation of different molecular weight urokinases labelled with $^{125}$I in the blood of beagle after intravenous injection.

Based on the results of studies performed on the pharmaceutical efficacy in vivo of the urokinase preparation and on the method for recovering such efficaseous urokinase, the present inventors have succeeded in developing a novel standardized urokinase preparation having a high biological efficacy which contains high molecular weight urokinase as major constituent.

An object of this invention is to provide a method for producing a thrombolytic preparation containing urokinase having a molecular weight of 54,000±10,000 as major constituent.

The method for producing urokinase having a molecular weight of 54,000±10,000 is not specific unless the yield is a matter of importance. Urokinase can be isolated in a known manner through several treatment steps including separation from urine, concentration and purification. The purified urokinase is subjected to a treatment used in separating and recovering an enzyme of prescribed molecular weight, such as fractionation by gel filtration, ion-exchange column technique, affinity chromatography or fractional precipitation.

The gel filtration is a simple method for recovering urokinase of a prescribed molecular weight and gives good results. The suitable materials for gel filtration include crosslinked dextran gel, polyacrylamide gel and agarose gel made to treat a substance having a molecular weight in the range of 1,000 to 150,000. The filter material is held in a column equilibrated with a low salt buffer solution of pH 5.5 to 9.5. An aqueous solution containing urokinase is developed on the column and the fraction containing urokinase having a molecular weight of 54,000±10,000 is recovered. Such a procedure is merely an example and not limitative.

The present inventors made studies on the improvement of the yield of urokinase having a molecular weight of 54,000±10,000 and, as the result, found that it is effective for the improvement of yield to keep in each treatment step the pH of an aqueous solution containing urokinase within the neutral or weakly alkaline range, preferably from 5.5 to 12, particularly in the dialysis step for the removal of salts. When this condition is satisfied, the stability of urokinase is secured and the urokinase having an intended molecular weight of 54,000±10,000 is recovered effectively without the decomposition taking place. The experimental example 1 given below suggests the above fact.

EXPERIMENTAL EXAMPLE 1

The interrelationship between pH and the ratio of residual urokinase activity as well as the molecular weight distribution:

Urokinase which had been recovered from human urine by adsorption on silica gel was fractionated with ammonium sulfate and the extract solution was adjusted to a urokinase potency of 9,800 IU. The resulting solution was dialyzed for 40 hours at 4° C. against an outer liquid of water, a 1 M sodium acetate buffer solution of pH 3.0, 4.0, 5.0, 6.0, 7.0, 8.0, 9.0, 11.0 or 12.0 or a 1/15 M phosphate buffer solution, while renewing the outer liquid at a time interval of 8 hours. After completion of the dialysis, the ratio of residual activity was assayed and molecular weight distribution was roughly evaluated by the molecular sieving by means of gel filtration technique. The ratio of residual activity found and the results of molecular weight estimation on urokinase fractions by reference to standard samples of known molecular weight were as summarized in Table 1.

TABLE 1

Interrelationship between pH and the ratio of residual activity as well as the molecular weight distribution.

| Run No. | pH of outer liquid | Activity after dialysis | Ratio of residual activity | Molecular weight distribution 33,000 ±10,000 | Molecular weight distribution 54,000 ±10,000 |
|---|---|---|---|---|---|
| Control | Extract solution | 9,800 | 100 | — | ++ |
| " | H₂O | 8,514 | 86 | ± | ± |
| 1 | 3 | 6,324 | 65 | ++ | — |
| 2 | 4 | 6,314 | 64 | ++ | — |
| 3 | 5 | 6,426 | 66 | + | + |
| 4 | 6 | 7,252 | 74 | — | + |
| 5 | 7 | 8,296 | 85 | — | ++ |
| 6 | 8 | 10,290 | 105 | — | ++ |
| 7 | 9 | 9,672 | 99 | — | ++ |
| 8 | 11 | 9,016 | 92 | — | ++ |
| 9 | 12 | 8,722 | 89 | — | ++ |

Note:
—undetectable;
±detectable;
+detectable to a considerable extent;
++detectable to a sufficiently great extent In the urokinase preparation obtained from human urine, there is the possibility of containing viruses which cause hepatitis, endemic and other diseases. In order to be administrable to man as a pharmaceutical, urokinase should undergo the treatment for virus inactivation, that is, the known heat treatment (55° to 65° C., for 9 to 11 hours) which is the simplest and the most reliable at present. During the heat treatment, it is also effective for the stability of urokinase to adjust the aqueous urokinase solution to pH 6–8 with a buffer solution, 0.01 to 0.3 M in salt concentration. An extremely high stabilizing effect against heat is obtained when a heat stabilizer selected from the group consisting of proteins, amino acids, saccharides and neutral salts is present in addition to the above-noted pH condition. Although not critical, the specific activity of urokinase is preferably 200 or higher, most preferably 1,000 or higher international units (IU) per mg. The amount of urokinase in the solution to be heat-treated is generally 0.001 to 5% (W/V), preferably 0.01 to 1% (W/V), in terms of protein. It is preferable to keep pH of the solution to be heat treated at 6 to 8 adjusting with a buffer solution, particularly a phosphate buffer solution, 0.01 to 0.3 M in salt concentration.

Under the above conditions, suitable heat stabilizers, if used, are amino acids such as glycine, lysine and arginine; saccharides such as sucrose and mannit; neutral salts such as sodium chloride; and proteins such as gelatin.

The lower limit of the amount of stabilizers to be added is normally 5% for glycine, sucrose and mannit, 0.1 M for lysine and arginine, 0.15 M for sodium chloride, and 0.1% in terms of protein for albumin and gelatin. Even when the amount is reduced below the lower limit, the stabilizer does not lose its effect abruptly but only gradually. There is no upper limit of the amount of stabilizer, unless removal of the stabilizer from the preparation is taken into account.

The temperature of virus inactivation treatment is 50° to 70° C., preferably 55° to 65° C. and the time of heating is 8 to 12 hours. The heat-treated urokinase, if necessary, is freed from salts and heat stabilizers by dialysis or the like. Highly purified urokinase is divided into vials and freeze-dried to obtain pharmaceutical preparations. In the case of crude urokinase, it is similarly made into pharmaceutical preparations after having been highly purified by use of well-known ion exchangers, urokinase specific adsorbents, or sepharose 4B.

In order to examine the effect of heating on the infectivity of viruses having possibility of existing in the urokinase preparation, heating experiments were run in the presence or absence of heat stabilizers. The viruses added to the aqueous urokinase solution were smallpox virus, mumps virus, measles virus, vesicular stomatitis virus, chikungunya virus, Japanese encephalitis virus, hepatitis B virus, rubeola virus, poliovirus, coxsackievirus and echovirus. The heat treatment was carried out at 60° C. for 10 hours during which the residual infectivity was tested at regular intervals. In ten hours, the infectivity was completely lost whether the heat stabilizer is present or not. These results suggest that the heat treatment according to this invention will exert an inactivation effect also on other viruses than those used in the above experiments. Experimental Examples 2 and 3 which suggest the above results are given below.

EXPERIMENTAL EXAMPLE 2

Dependence of the stability of urokinase in heat treatment on pH:

A phosphate buffer solution was added in various concentrations to an aqueous urokinase solution [specific activity, 15,000 IU/mg; protein concentration, 0.02% (W/V)] to prepare samples of urokinase solutions having pH of 4, 5, 6, 7, 8, 9 and 10. Each sample was heated at 60° C. for 10 hours and the residual activity was compared. After the heat treatment, the heat stabilizer was removed by dialysis and the urokinase activity was assayed to calculate the ratio of residual activity by taking the specific activity before heating as 100%. As shown in FIG. 1, urokinase retained 52%, 65% and 50% of initial activities at pH 7, 8 and 9, respectively, indicating that the adjustment of the aqueous urokinase solution to pH in the range of 6 to 8 is effective.

EXPERIMENTAL EXAMPLE 3

Effect of the heat stabilizers:

In this Experimental Example 3, by using various heat stabilizers, each stabilizing effect against heat was compared with one another. After the heat treatment, the heat stabilizer was removed by dialysis and the ratio of residual activity was determined by taking the specific activity before heat treatment as 100%. The results obtained were as shown in Table 2. The viruses used in the experiment were the same as described in Experimental Example 2. In Table 2, "control (1)" is the case where the heat stabilizer was absent and pH was adjusted to 6.8 with 0.1 M phosphate buffer solution and "control (2)" is the case where the phosphate buffer solution was not added and, hence, pH was not adjusted. The residual urokinase activities were 65-75%, 78% and 79% in the presence of glycine, lysine and arginine, respectively, 75-78%, 78% and 71-75% in the presence of sucrose, mannitol and sodium chloride, respectively, and 88-100% in the presence of gelatin, indicating that all of said substances are effective heat stabilizers. When the aqueous urokinase solution was adjusted to pH 6.8, urokinase retained 65% of the initial activity in the absence of a heat stabilizer, indicating that the adjustment of the urokinase solution to pH 6 to 8 is effective in stabilizing the activity.

TABLE 2

| Heat stabilizer | | Ratio of residual urokinase activity, % | Infectivity of residual virus |
|---|---|---|---|
| Type | Concentration, % | | |
| Glycine | 5 | 65 | |
|  | 10 | 70 | None |
|  | 15 | 75 | |
| Lysine | 0.1 M | 78 | " |
| Arginine | 0.1 M | 79 | " |
| Sucrose | 5 | 75 | |
|  | 10 | 77 | " |
|  | 15 | 78 | |
| Mannit | 5 | 73 | |
|  | 10 | 73 | " |
| Sodium chloride | 0.15 M | 71 | " |
|  | 0.3 M | 75 | |
| EDTA | 0.1 | 23 | " |
| Gelatin | 0.5 | 88 | |
|  | 1.0 | 91 | " |
|  | 3.0 | 89 | |
| Control (1) (Urokinase only) | — | 65 | " |
| Control (2) (No buffer solution) | — | 0 | " |

Tests for thrombolytic activity, half-life in the blood after intravenous administration, stability, toxicity, administration dose, and way of administration in vitro and vivo were performed on urokinase having a molecular weight of 54,000±10,000. The experimental methods and the results are described below.

EXPERIMENTAL EXAMPLE 4

Determination of thrombolytic activity by the method of Chandler's loop:

Purified urokinase was fractionated into fractions having, respectively, molecular weights of 33,000±10,000 (33,000 for the most part), 54,000±10,000 (54,000 for the most part), and about 100,000. The fraction having a molecular weight of about 100,000 was found in a very small amount and seemed to be an associated product of urokinase having a molecular weight of 54,000. The recovery of this fraction from urine is commercially impossible. Each fraction was dissolved in physiological saline to prepare the following samples of varied potencies: sample (1), 187.75 IU/ml; sample (2), 37.5 IU/ml; sample (3), 75.0 IU/ml; sample (4), 150 IU/ml; sample (5), 300 IU/ml and a control sample (physiological saline).

The potency in IU unit is determined by a two-step method in vitro, which comprises allowing the urokinase preparation under test to act on purified plasminogen, used as substrate, to form plasmin, then decomposing the secondary substrate fibrin by the action of plasmin thus formed, and calculating the potency from the time of dissolution of the fibrin [Pharmaceuticals Research, 5 (3), 295-308 (1974)]. The relationship between the IU unit and the conventional plug unit [B.B.A., 24, 278-282 (1975)] is expressed by 5,000 plug unit=6,000 IU.

The formation of thrombus and the determination of dissolution ratio were carried out in the following way:

In a piece of plastic tubing (3 mm in inner diameter and 270 mm in length), were placed 1 ml of fresh blood containing 3.8% of a citrate and 0.1 ml of 0.25 M calcium chloride solution. The tubing was sealed at both ends to form a loop. A thrombus was formed by rotating, at 12 r.p.m., the sealed tube for 30 minutes at 37° C. Into the loop was injected one of the urokinase sample solutions or the control sample. The tube was again rotated at 12 r.p.m. for 4 hours at 37° C. The residual thrombus taken out of the tube was fixed overnight with Bovin's solution (prepared by mixing together 75 ml of saturated aqueous solution of picric acid, 25 ml of commercial formalin and 5 ml of glacial acetic acid), and the weight of thrombus was determined to examine the interrelationship among the IU potency, molecular weight and thrombolytic activity. The thrombolytic activity of urokinase was expressed in terms of weight ratio of the average thrombus weight of the group containing urokinase to the average thrombus weight of the control group (physiological saline group). This ratio was herein referred to as "thrombolytic ratio (in %)" and shown in Table 3.

TABLE 3

| | Relationship between the molecular weight of urokinase and the thrombolytic ratio (%). | | | | |
|---|---|---|---|---|---|
| Molecular weight of urokinase | Sample (1) | Sample (2) | Sample (3) | Sample (4) | Sample (5) |
| 100,000 | 0 | 2 | 62 | 82 | 80 |
| 54,000 | 0 | 1 | 63 | 83 | 81 |
| 33,000 | 0 | 1 | 13 | 65 | 72 |

From the results shown in Table 3, it was found that urokinase having a molecular weight of 54,000 is excellent in thrombolytic activity, whereas urokinase having a molecular weight of 33,000 has a thrombolytic activity as small as less than half that of high molecular weight urokinase. Although the test for thrombolytic activity by the method of Chandler's loop is carried out in vitro, it is recognized as a simple and convenient testing method which most approximates the test in vivo [J. Exp. Physiol., Vol. XLIV (4), 377-384 (1959)] and is believed to be able to represent sufficiently the performance of urokinase having a molecular weight of 54,000±10,000 used in this invention.

The results obtained above showed a surprising fact that urokinase preparations heretofore evaluated to be of the same potency, as assayed by the conventional test tube method, plating method or two-step method (Pharmaceuticals Research, loc. cit.), exhibit quite different thrombolylic activity depending upon the molecular weight of urokinase.

EXPERIMENTAL EXAMPLE 5

Thrombolytic effect in vivo (in rats):

Following the method of Y. Sasaki [Thrombosis Res., 9, 513 (1976)] and R. N. Chakravart [Atherosclerosis, 21, 349 (1975)], the fibrinolytic action of urokinase in vivo was examined by use of rats.

Human fibrinogen was labelled with $^{125}I$ by the method of Greenwood et al. [Biochem. J., 89, 114 (1963)] to prepare $^{125}I$-human fibrinogen. Four milliliters of a 0.4% $^{125}I$-human fibrinogen solution was admixed with 200 IU of human thrombin and left standing for about 60 minutes at room temperature to form fibrin. After sufficient removal of water with filter paper, the fibrin was washed thoroughly with physiological saline on a filter paper. The filter paper carrying the fibrin was cut to small pieces, admixed with 4 ml of physiological saline, and triturated sufficiently to prepare a dispersion of $^{125}I$-human fibrin, 5 to 10μ in particle diameter. The fibrin content of the dispersion was 12 mg/ml on wet basis and the $^{125}I$ radioactivity was $2.93 \times 10^6$ c.p.m. Wistar strain rats (male, weighing each 250 g) were each administered through caudal vein with 1 ml of the dispersion followed by 30,000 IU of urokinase having a molecular weight of 54,000 or 33,000. Thereafter, at regular time intervals, each 0.3 to 0.5 ml of blood was collected from the carotid artery into a test tube containing one drop of aprotinin solution (15,000 KIE/ml), an antiplasmin, and left standing for 2 hours at room temperature. A 0.05 ml portion of serum separated from the blood was assayed for the fibrin decomposition products (FDP) by measuring the radioactivity. Percentage formation of $^{125}I$-FDP in blood was determined with the lapse of time from the value of radioactivity per ml of the serum and the total amount of circulating serum (31.1 ml/kg), by taking the radioactivity of administered fibrin as 100%. The results obtained were as summarized in Table 4.

TABLE 4

Percentage formulation of $^{125}I$-FDP in blood based on administered dose (urokinase 30,000 IU per rat; intravenous injection)

| Time elapsed after administration, minute | High mol. wt. urokinase (mol. wt. 54,000) | Low mol. wt. urokinase (mol. wt. 33,000) | Physiological saline |
|---|---|---|---|
| 0 | 2.5 | 2.4 | 2.4 |
| 15 | 27.5 | 15.6 | 5.3 |
| 30 | 38.3 | 23.2 | 6.8 |
| 45 | 18.2 | 16.1 | 9.7 |
| 60 | 20.7 | 13.2 | 15.2 |
| 75 | 16.5 | 16.9 | 1.0 |

It is seen from Table 4 that a high-molecular weight urokinase produces FDP earlier than a low-molecular weight urokinase and both the fibrin decomposition rate and the amount of FDP produced are higher in the case of the former urokinase.

From the above results it was found that a high-molecular weight urokinase exhibits in vivo a higher fibrinolytic activity and a higher thrombolytic activity.

EXPERIMENTAL EXAMPLE 6

Influence of molecular weight on attenuation of administered urokinase in blood:

Urokinase preparations of different molecular weights were labelled with $^{125}I$ by the method of Greenwood et al. [Biochem. J., 89, 114 (1963)]. The labelled urokinases were administered by intravenous injection to the groups of test animals and the attenuation of urokinase in the blood was compared.

Urokinases with a molecular weight of 54,000 (high molecular weight urokinase; specific activity, 100,000 IU/mg of protein) and 33,000 (low molecular weight urokinase; specific activity 160,000 IU/mg of protein) were labelled with $^{125}I$ by the method of chloramine T [Biochem. J., 89, 114 (1963)]. The specific radioactivities were $1.28 \times 10^7$ c.p.m./mg of protein in the former and $2.24 \times 10^7$ c.p.m./mg of protein in the latter. The test animal used was three beagles (male, each weighing 12 to 15 kg) per group.

The administration dose was 1,000 IU/kg in both cases of high and low molecular weight urokinases, and both were administered through the paratid vein. At regular time intervals after the administration, each 5 ml of blood was collected from the vein of front paw by using a syringe containing 0.5 ml of a 3.8% sodium citrate solution. The plasma was separated from the blood by centrifugation and assayed for the radioactivity with a scintillation counter (Packard Co.). The results obtained were as shown in FIG. 2. The decay curve H of the high molecular weight urokinase in blood runs more slowly than the curve L of the low molecular weight urokinase, the half-life of the former urokinase having been twice that of the latter.

EXPERIMENTAL EXAMPLE 7

Molecular weight and the stability of enzymatic activity:

By using commercial urokinase, the relationship between the molecular weight and the stability of enzymatic activity was examined. The commercial urokinase was fractionated into fractions of the molecular weight of 20,000, 33,000, 54,000 and 100,000 by gel filtration (Sephadex G-75; a 70 mM phosphate buffer solution of pH 8.0; $2.6 \times 80$ cm column). Each fraction was adjusted to 10,000 IU/ml (aqueous solution), preserved at 4° C. or $-10°$ C., and change in activity with time was examined. In Table 5 is shown the time required until the 50% residual activity was reached.

From the above experiment, it was found that the stability of the urokinase having a molecular weight of 54,000 was about three times as large as that of the low molecular weight urokinase.

TABLE 5

Time elapsed until 50% residual activity is reached.

| Storage temperature | Molecular weight | | | |
|---|---|---|---|---|
| | 20,000 | 33,000 | 54,000 | 100,000 |
| 4° C. | <1 day | 5 days | 15 days | 11.5 days |
| −10° C. | 2.5 days | 6 days | >10 days | >20 days |

EXPERIMENTAL EXAMPLE 8

Toxicity test:

For toxicity test, five mice and five guinea pigs (each weighing about 20 g, well-nourished and healthy) were used. High molecular weight urokinase having a molecular weight of 54,000 (15,000 IU) was dissolved in 25 ml of water for injection. Each mouse and each guinea pig were subcutaneously administered with, respectively, 0.5 ml and 5 ml of the above urokinase solution. In 7 days after the administration, no nortal case was observed. In this case, the amount of urokinase to be administered was 300 IU per one mouse and 3,000 IU per one guinea pig, respectively.

In using clinically the preparation of this invention, 50 to 30,000 IU of the urokinase preparation of this invention is dissolved in 0.5 to 5 ml of water for injection (Japanese Pharmacopoeia) and administered, making proper allowances for age, symptom, and progress of the disease, by intravenous injection, intravenous drip, drop-by-drop infusion, subconjunctival injection, or retrobulbar injection.

The thrombolytic preparation of this invention containing as major ingredient urokinase of a molecular weight of 54,000±10,000 is a preparation having uniform molecular weight, excellent preservability and high thrombolytic activity, which permits compounding and dosage to be standardized. Moreover, the thrombolytic preparation of this invention exhibits sufficient thrombolytic effect at a low potency dose level. Thus, the present invention provides a pharmaceutical preparation useful in the therapeutic field.

The invention is further illustrated below with reference to Examples.

EXAMPLE 1

Fresh urine collected from male adults was adjusted to pH 7.2. Five liters of the adjusted urine was fed to the top of a column packed with 50 ml of L-arginine-agarose (equilibrated with a 2% sodium chloride solution of pH 7.2) to adsorb urokinase on the column. The column was washed with 100 ml of a 2% sodium chloride solution of pH 7.5 and the urokinase was eluted with a downward stream of 50 ml of a 1 M solution of sodium chloride of pH 6.0. The eluate was concentrated to about 10 ml and fed to a column, 2.6×80 cm, packed with Sephadex G-75 (Pharmacia Co.; equilibrated with a 70 mM phosphate buffer solution of pH 8.0) and subjected to gel filtration at a flow rate of 20 ml/hour, using the same buffer solution as used in equilibration. The filtrate was collected in 0.5 ml portions and the fractions containing urokinase having a molecular weight of 54,000±10,000 were recovered. The recovered aqueous solution containing urokinase was analyzed by the simplified method for molecular weight determination by the SDS-electrophoresis in polyacrylamide gel [Colowick-Kaplan, Method in Enzymology, 26, 3 (1972)]. The molecular weight was confirmed by a single peak correspoinding to that of the standard urokinase sample of a molecular weight of about 54,000. The aqueous solution was dialyzed against physiological saline and freeze-dried to obtain a sample of urokinase having a specific activity of 17,000 IU/mg.

EXAMPLE 2

The urokinase (specific activity 17,000 IU/mg) obtained in Example 1 was dissolved in a 0.05 M phosphate buffer solution at pH 7.0 to obtain 20 liters of an aqueous urokinase solution [3,000 IU/ml; protein content 0.02% (W/V)]. The solution was heated at 60° C. for 10 hours, then quenched in ice water and filtered through a bacterial filter. The filtrate was divided into 2 ml portions and freeze-dried to obtain a urokinase preparation with viruses inactivated.

EXAMPLE 3

To 5 liters of an aqueous urokinase solution [10,000 IU/ml; protein content 2.5% (W/V)] prepared by dissolving crude urokinase (specific activity 400 IU/mg) in a 0.1 M phosphate buffer solution of pH 6.8, was added 0.3 M of sodium chloride dissolved in the same buffer solution as used before. The resulting solution was sufficiently stirred and then heated at 60° C. for 10 hours. The solution thus treated was dialyzed against a 0.0075 M sodium chloride solution of pH 7.0 through a dialysis tube made by Visking Co. The dialyzed aqueous solution of crude urokinase was fed to a column packed with 1 kg of powdered bentonite which was equilibrated with a 0.0075 M aqueous sodium chloride solution of pH 7.0. The urokinase was adsorbed on the bentonite while impurities passed through the column unadsorbed. The impurities adhered to the bentonite were washed out with a 0.1 M sodium chloride solution of pH 9.0. The urokinase was eluted with a 2.0% (W/V) aqueous solution of 6,9-diamino-2-ethoxyacridine lactate hydrate.

The resulting urokinase solution contained about 70% of the urokinase initially present in the starting material and had a purity of 11,000 IU/mg. After having been dialyzed against physiological saline, the urokinase solution was filtered through a bacterial filter, divided into 2 ml portions and freeze-dried to obtain a urokinase preparation with viruses inactivated.

The aqueous urokinase solution recovered above was analyzed by the simplified method for molecular weight determination by the SDS-electrophoresis in polyacrylamide gel [Colowick-Kaplan, Method of Enzymology, 26, 3 (1972)]. The molecular weight was confirmed by a single peak corresponding to that of the standard urokinase sample of a molecular weight of about 54,000.

What is claimed is:

1. In a method for producing a thrombolytic preparation from a fresh urine or a crude urokinase solution which consists essentially of (1) adsorbing urokinase on a selected adsorbent, (2) eluting and recovering the absorbed urokinase, (3) heat-treating the recovered urokinase solution at a temperature of 50° to 70° C. for 8 to 12 hours, and (4) subjecting the heat-treated solution to dialysis, the improvement comprising carrying out the heat-treatment step at pH 6 to 8 and carrying out the dialysis step at pH 5.5 to 12 to recover urokinase having a molecular weight of 54,000±10,000.

2. A method for producing a thrombolytic preparation according to claim 1, comprising adding a heat-stabilizer for urokinase selected from the group consisting of glycine, lysine, arginine, sucrose, mannitol, sodium chloride and gelatin to the aqueous solution containing urokinase.

3. A method according to claim 2 wherein the stabilizer is selected from the group consisting of arginine, sucrose, mannitol, sodium chloride and gelatin.

* * * * *